(12) United States Patent
Ziaja et al.

(10) Patent No.: US 8,226,060 B2
(45) Date of Patent: Jul. 24, 2012

(54) CONNECTION DEVICE

(75) Inventors: Hermann Ziaja, Burgthann (DE);
Juergen Brecht, Graben-Neudorf (DE);
Christian Strauss, Halle/Saale (DE)

(73) Assignee: CWW-med AG, Zug (CH)

( * ) Notice: Subject to any disclaimer, the term of this patent is extended or adjusted under 35 U.S.C. 154(b) by 233 days.

(21) Appl. No.: 12/690,951

(22) Filed: Jan. 21, 2010

(65) Prior Publication Data

US 2010/0181446 A1    Jul. 22, 2010

Related U.S. Application Data

(63) Continuation of application No. PCT/EP2008/005997, filed on Jul. 22, 2008.

(30) Foreign Application Priority Data

Jul. 23, 2007  (DE) .......................... 10 2007 035 922

(51) Int. Cl.
*E04G 3/00* (2006.01)

(52) U.S. Cl. ............................... 248/276.1; 248/288.51

(58) Field of Classification Search ............... 248/276.1, 248/288.51, 274.1, 278.1, 288.31, 159, 160, 248/158

See application file for complete search history.

(56) References Cited

U.S. PATENT DOCUMENTS

| | | | |
|---|---|---|---|
| 3,737,130 A | 6/1973 | Shiraishi | |
| 4,807,618 A | 2/1989 | Auchinleck et al. | |
| 5,918,844 A | 7/1999 | Ognier | |
| 6,220,556 B1 * | 4/2001 | Sohrt et al. ................. | 248/279.1 |
| 6,352,227 B1 * | 3/2002 | Hathaway .................... | 248/160 |
| 7,646,161 B2 * | 1/2010 | Albu-Schaffer et al. ... | 318/568.2 |
| 2008/0197256 A1 * | 8/2008 | Hirschhorn ................ | 248/276.1 |
| 2009/0090831 A1 * | 4/2009 | Henning et al. ........... | 248/278.1 |

FOREIGN PATENT DOCUMENTS

| | | |
|---|---|---|
| DE | 2 048 592 | 2/1972 |
| DE | 295 11 900 U1 | 11/1995 |
| DE | 195 26 915 A1 | 2/1997 |
| DE | 198 45 625 C1 | 5/2000 |
| DE | 102 34 271 A1 | 2/2004 |
| DE | 10 2005 027 882 B3 | 12/2006 |
| EP | 0 868 885 A1 | 10/1998 |
| FR | 2 660 714 | 10/1991 |
| FR | 2 711 506 | 5/1995 |

* cited by examiner

*Primary Examiner* — Ramon Ramirez
(74) *Attorney, Agent, or Firm* — Harness, Dickey & Pierce, P.L.C.

(57) ABSTRACT

A connection device for adjustably connecting a surgical apparatus connected to a first end of the connection device to an attachment part on a stationary device, such as an operating table, which can be connected to a second end of the connection device. The connection device has a first holding arm and a second holding arm, connected to the first holding arm in a hinged fashion via a ball and socket joint. A clamping apparatus is provided for detachably clamping the ball of the ball and socket joint in the ball and socket joint receptacle. A hydraulic apparatus is also provided which, when operated, loads the clamping apparatus with a force opposing the clamping force. Further, a clamping force transformation apparatus transforms the force applied by the clamping apparatus into a larger clamping force.

14 Claims, 4 Drawing Sheets

CONNECTION DEVICE

CROSS REFERENCES TO RELATED APPLICATIONS

This application is a continuation of copending international patent application PCT/EP2008/005997 filed on Jul. 22, 2008 and designating the U.S., which was published in the German language and claims priority of German patent application DE 10 2007 035 922.7 filed on Jul. 23, 2007. The entire contents of these priority applications are incorporated herein by reference.

BACKGROUND OF THE INVENTION

The present invention relates to a connection device for adjustably connecting a surgical apparatus, preferably a head support, which can be connected to a first end of the connection device to an attachment part on a stationary device, preferably an operating table, which can be connected to a second end of the connection device, the connection device having a first holding arm, a second holding arm, connected to the first holding arm in a hinged fashion, with a ball and socket joint receptacle being assigned to the first holding arm and a ball and socket joint ball being assigned to the second holding arm, which together form a ball and socket joint, a clamping apparatus for the detachable clamping of the ball and socket joint ball in the ball and socket joint receptacle, the latter having a clamp-type socket which is assigned to the ball and socket joint ball and acted on by a clamping force via a pretensioning element in order to attain the clamping, and a first hydraulic apparatus which can be actuated, is assigned to the clamping apparatus and, when operated, loads the clamping apparatus with a force opposing the clamping force, with the hydraulic apparatus having a hydraulic cylinder and a hydraulic piston which is arranged such that it can be displaced therein and connected to the clamping apparatus.

Connection devices of the abovementioned type are known. For example, the document DE 102 34 271 A1 shows such a device. The documents FR 2 660 714 A1 or EP 0 868 885 A1 also show connection devices which have ball and socket joints. Finally, reference should be made to the document DE 10 2005 027 882, which likewise discloses a connection device. The document DE 198 45 625 C1 also shows a connection device.

Such connection devices can be used to fix a surgical head support to an attachment part which in turn is attached to the operating table. The head support itself is used to keep the head of a patient in a defined position in respect of the operating table during a neurosurgical intervention.

The surgical head support is generally attached to a support part such that it can rotate about two axes and the support part in turn is attached to the connection device such that it can rotate about one rotational axis. The attachment part attached to the operating table is likewise held on the connection device such that it can rotate about one axis.

In DE 198 46 625 C1 (specified above), the clamping of the attachment part and the support part within the connection device is achieved mechanically by clamping using a lever which can be actuated manually.

In the meantime, hydraulic clamps have also been disclosed, for example by the above-mentioned DE 10 2005 027 885 from the assignee of the present applicant.

The reliability of the clamping, be it mechanical or hydraulic, is very important because an inadvertent release of the clamping can have fatal consequences which, in a worst-case scenario, can lead to the death of the patient. Moreover, operating the connection device must be simple to disburden the operator.

SUMMARY OF THE INVENTION

Against this backdrop, it is the object of the present invention to develop the connection device mentioned initially such that, on the one hand, a very high clamping force and thus a reliable connection is possible and, on the other hand, it can easily be handled by the operator.

The mentioned connection device achieves this object by the fact that provision is made for a clamping force transformation apparatus which is arranged between the pretensioning element and clamp-type socket and transforms the force applied by the pretensioning element into a larger clamping force acting on the clamp-type socket.

In other words, this means that, unlike the previous prior art, it is not only a spring which ensures that the clamping force is sufficient to keep the two holding arms in their set position in respect of one another, but that the clamping force transformation apparatus transforms this clamping force into a larger force which then acts on the clamp-type socket and, consequently, on the ball and socket joint ball. A transformation of the force usually means that the spring path is significantly increased compared to the path of the clamp-type socket.

The advantage of this clamping force transformation apparatus lies in the fact that it is possible to generate a very high clamping force acting on the ball and socket joint ball without the dimensions of the spring, and therefore the entire holding arm, becoming much larger. Hence, the connection device still has a very small and compact design.

The first hydraulic apparatus is provided to release this fixed clamping; it is actuated by the operator using, for example, a foot pedal and generates a force which opposes the clamping force.

As a result of the fact that the clamping force does not have to be applied only by the pretensioning element, usually a spring, very much higher clamping forces can be implemented and so the clamping itself becomes significantly more reliable. Using the hydraulic apparatus, the clamping can be easily detached without the operator having to put in much effort and so a repositioning of the head support can be performed easily and quickly. In particular, the operator is not forced to apply the clamping force manually onto the connection device using a lever, for which said operator would usually have to use both hands. Rather, the connection device according to the invention enables the operator to only require one hand (if at all) in order to actuate the hydraulic apparatus.

Moreover, this ensures that the clamping of the ball and socket joint ball in the ball and socket joint receptacle is not lost even if the first hydraulic apparatus fails because the hydraulic apparatus is only provided for the release.

In a preferred development, the clamping force transformation apparatus has a second hydraulic apparatus with a cylinder and a piston which is arranged such that it can be displaced therein, with the clamp-type socket forming the piston, and the clamping apparatus has an actuation element which projects into the cylinder and the displacement of which causes a displacement of the clamp-type socket.

In other words, this means that the clamping force transformation apparatus operates on the basis of a hydraulic cylinder, wherein the actuation element and the clamp-type socket are coupled using a hydraulic fluid. As a result of the dimensions of the actuation element and the clamp-type socket, a long path of the actuation element in the longitudinal direction with a small amount of force is converted into a movement of the clamp-type socket with a short path in the longitudinal direction but with a large amount of force. By immersing the actuation element into the interior space of the cylinder, the clamp-type socket is moved so far that the volume increase of the interior space of the cylinder corresponds to the volume of the actuation element projecting therein.

In a preferred development, the first hydraulic apparatus has a stop element which projects into the hydraulic cylinder and limits the displacement path of the piston.

In other words, this means that the path to release the clamp-type socket is limited by the stop element. The advantage of this is that the path to releasing the clamp-type socket can be set to a minimal value as a result of a limitation and so, one the one hand, only a small amount of hydraulic fluid has to flow into the first hydraulic apparatus and, on the other hand, the clamping is again attained very quickly if the hydraulic pressure is removed.

This can achieve very precise and quick positioning.

In a preferred development, the stop element can be adjusted from the outside, the stop element having an outer tube-shaped section with a female thread and an inner section with a male thread which interact such that a rotation of the inner section displaces the outer section in the longitudinal direction. Furthermore, it is also preferable for provision to be made for a worm drive, the worm of which can be actuated from the outside and interacts with a gearwheel attached to the inner section of the stop element.

Using these measures, it is possible to adjust the stop element in the longitudinal direction from the outside in a particularly easy and precise fashion.

In a preferred development, each holding arm has a cylindrical housing in which the clamping apparatus and the first and the second hydraulic apparatus are housed. The clamping apparatus preferably has a flange-like section on which one end of the pretensioning element, in particular a spring, is supported, while the other end of the pretensioning element is supported on the housing.

These measures were found to be particularly advantageous from a design point of view.

In a preferred development, the ball and socket joint receptacle can be attached, in particular screwed, to one end of a holding arm. It is furthermore preferred that the ball and socket joint ball can be attached, in particular screwed, to the other end of a holding arm.

The advantage of these measures is that the holding arms can quickly be adapted to different circumstances because, for example, a ball and socket joint ball can quickly be replaced by another component at one end of a holding arm, for example by a component for attaching the head support.

In a preferred development, at least three holding arms are interconnected in a hinged fashion.

The degree of adjustability of, for example, a head support can be increased with the aid of a plurality of holding arms interconnected in a hinged fashion.

Further advantages and refinements of the invention emerge from the description and the attached drawing.

It goes without saying that the features which are mentioned above and yet to be explained below can be used not only in the respectively specified combination, but also in other combinations or on their own without departing from the scope of the present invention.

In this context, reference is particularly made to the fact that the abovementioned stop element in the first hydraulic apparatus can also be used without the clamping force transformation apparatus according to the invention. That is to say, it is not a necessary component of the clamping force transformation apparatus, but can also be advantageously used in a connection device without such a clamping force transformation apparatus.

BRIEF DESCRIPTION OF THE DRAWINGS

The invention will now be explained in more detail on the basis of an exemplary embodiment and with reference to the attached drawing, in which.

DETAILED DESCRIPTION OF PREFERRED EMBODIMENTS

Figure 1:
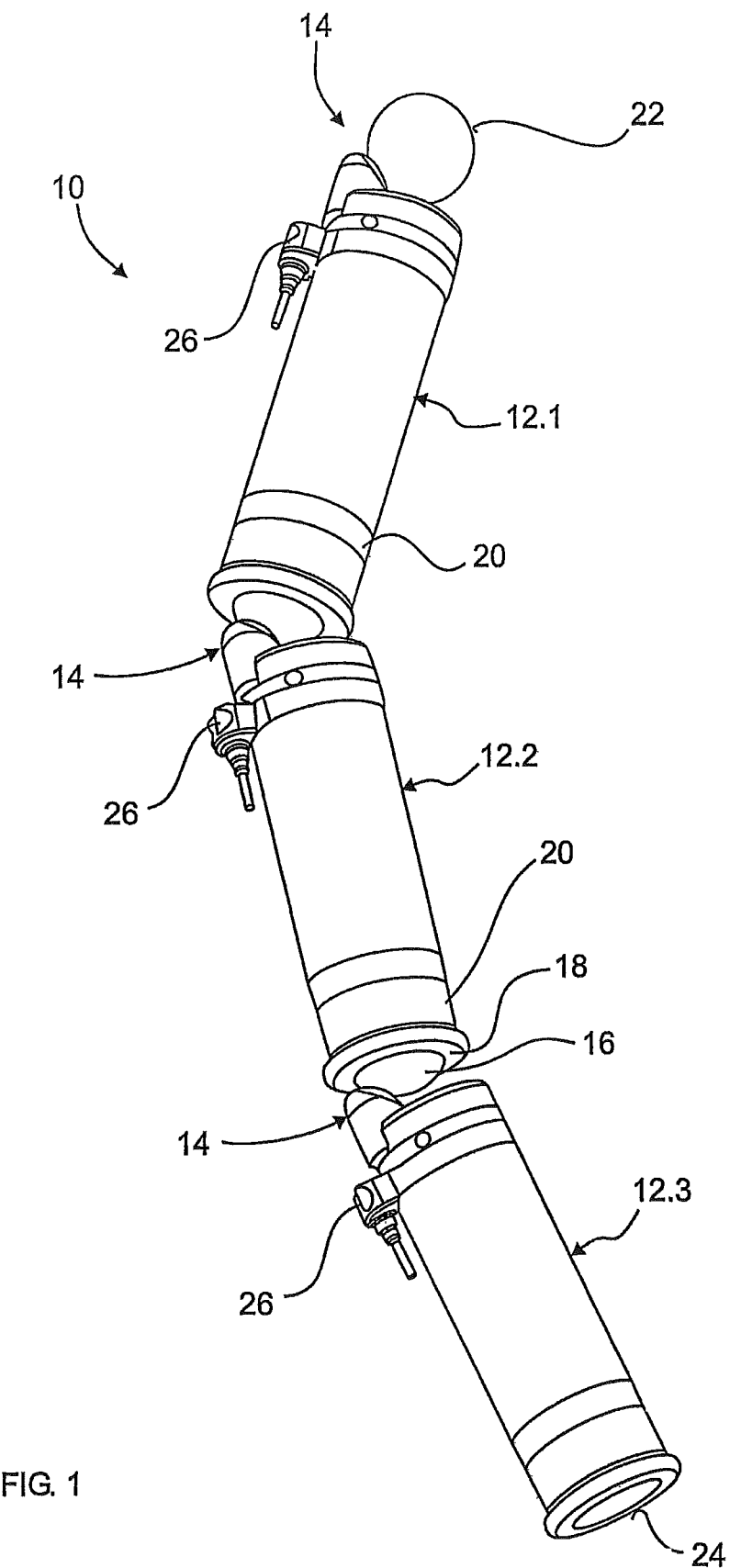
FIG. 1 shows a schematic perspective illustration of a connection device with three holding arms which are interconnected in a hinged fashion.

FIG. 1 shows a schematic illustration of a connection device characterized by the reference sign 10. The connection device 10 comprises, in an exemplary fashion, three holding arms 12.1, 12.2 and 12.3 which are interconnected in a hinged fashion. The number of utilized holding arms 12 can also equal two or be more than three.

The connection device 10 is used to attach a surgical apparatus, preferably a so-called head support, to an attachment part on a stationary apparatus, preferably an operating table, such that the head support can be adjusted and positioned by the hinged connection of the individual holding arms 12. The head support can, for example, be attached to one end 22 of the connection device, while the opposite end 24 of the connection device 10 is then connected to the operating table.

The hinged interconnection of the individual holding arms 12 is effected by ball and socket joints 14 which comprise a ball and socket joint ball 16 situated in a ball and socket joint receptacle 18 of the adjacent holding arm. The holding arm 12 can both be rotated about the longitudinal axis thereof, defined by a cylindrical housing 20, and be pivoted in all directions by means of this ball and socket joint 14. A device is provided in the interior of the cylindrical housing 20 of a holding arm and it clamps the ball and socket joint 14 such that the corresponding holding arm is fixedly adjusted and can no longer be moved. This device is described in due course with reference to FIGS. 2 and 3.

Finally, FIG. 1 also shows that a connection 26 is provided on the cylindrical housing 20 of each holding arm 12; said connection serves as a hydraulic connection and allows the attachment of a hydraulic tube. This hydraulics can effect the abovementioned clamping or releasing of the clamping of the ball and socket joint. A foot switch is usually provided for this purpose; however, it is not illustrated in the figures. The foot switch allows the users of the connection device to increase the hydraulic pressure introduced into the corresponding holding arm 12 via the hydraulic connection 26 in order to thereby release the clamping. This is required for adjusting and setting the surgical apparatus affixed to the end 22 of the connection device. Once the hydraulic pressure is removed, the ball and socket joints are then in turn clamped and so the set position can be maintained. It is customary for all three hydraulic connections 26 illustrated in FIG. 1 to be connected to one foot switch, with, however, other solutions also being feasible.

The design of a holding arm 12 will be explained in an exemplary fashion in the following text for the holding arm 12.1 on the basis of FIGS. 2 and 3. In this context, it should be noted that the design of the other holding arms 12.2 and 12.3 is identical to the design of the holding arm 12.1.

Figure 2:
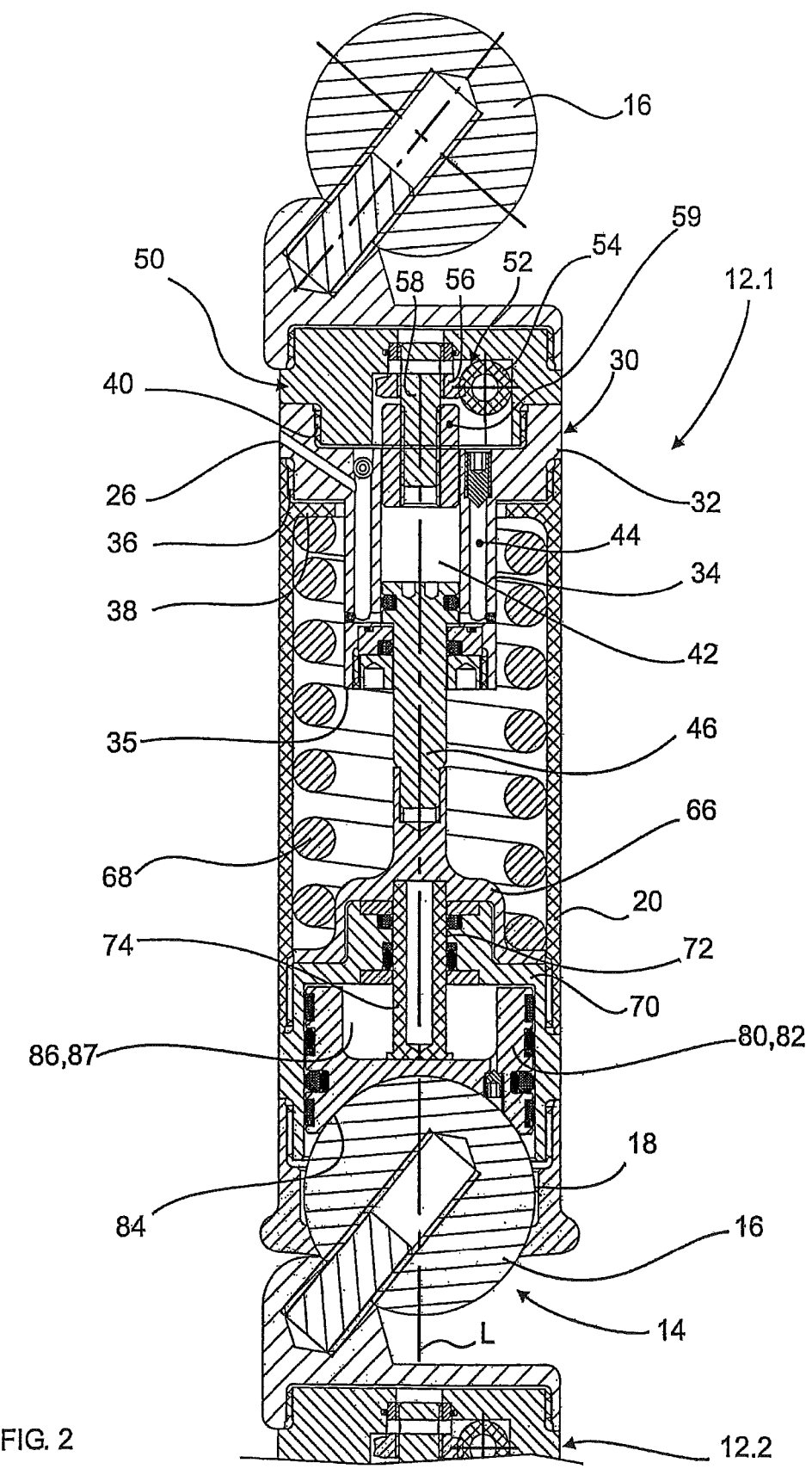
FIG. 2 shows a cross sectional view of a holding arm of the connection device in the clamped state.
Figure 3:
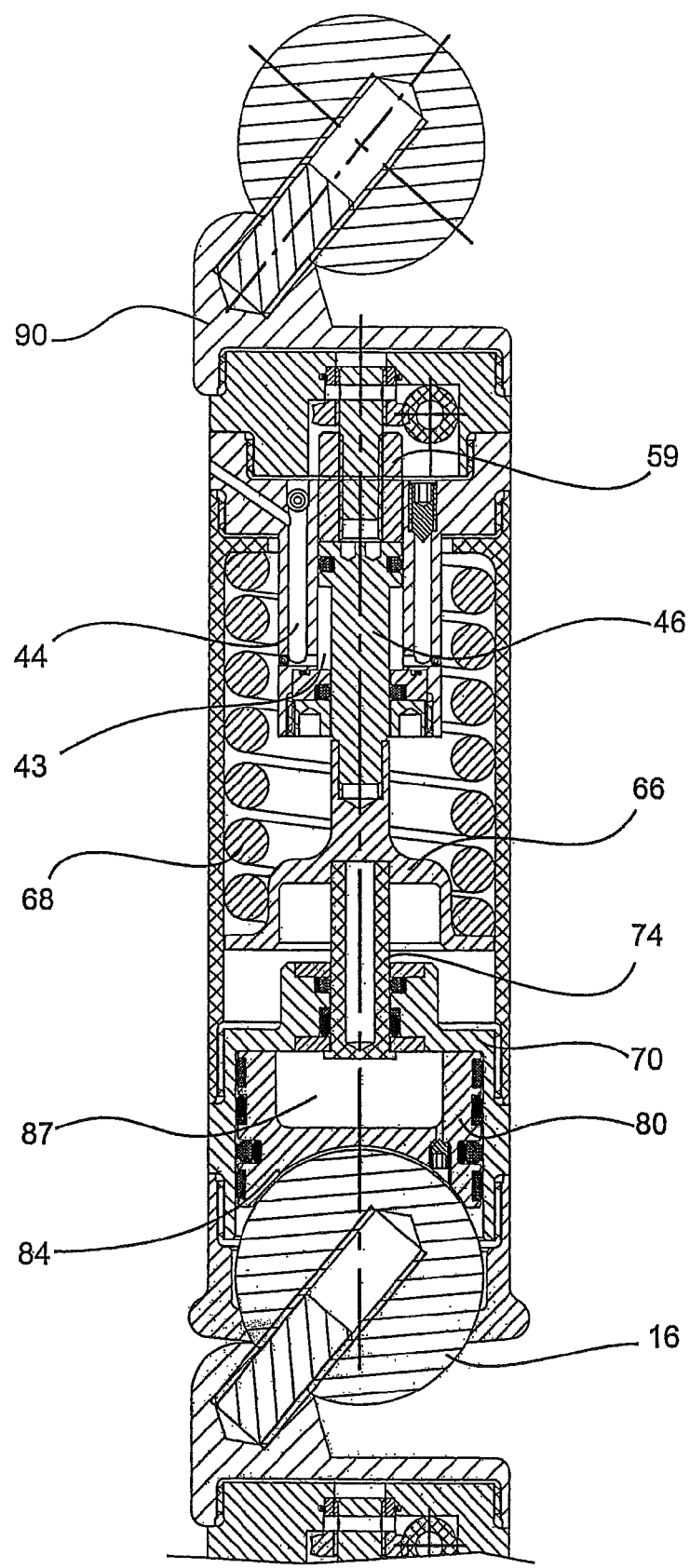
FIG. 3 shows a schematic sectional illustration of a holding arm in an opened, i.e. not clamped, state.

In FIGS. 2 and 3, the holding arm 12.1 is shown in a sectional illustration and in two different states, namely in a clamped position (FIG. 2) and in an adjustment position (FIG. 3).

FIG. 2 shows that the holding arm 12.1 has a cylindrical housing 20, with a hydraulic unit 30 being placed on the end of the housing which is at the top (in FIG. 2). This hydraulic unit 30 comprises the hydraulic connection 26 already mentioned above and forms a cylindrical cover 32 which closes off the cylindrical housing 20 toward the top. The cylindrical cover 32 is inserted, preferably screwed, into a receptacle 36 in the housing 20 and is situated on a flange-like section 38 of the housing 20 or is separated therefrom by a small distance.

A tube-like continuation 34 is attached to, or is an integral part of, the cylindrical cover 32 and it projects into the interior space of the housing through an opening of the flange-like section 38 of the housing 20.

This tube-like continuation 34 is closed off by a cover 35 at the lower end thereof and it forms a hydraulic cylinder 42. In addition to the cylindrical interior space, the tube-like continuation 34 has an annular space 44 which has a fluidic connection to the hydraulic connection 26 and the hydraulic interior space 43 (cf. FIG. 3).

The upper part of the hydraulic cylinder 42 is closed off by a stop unit 50 which is inserted, preferably screwed, into a bowl-shaped receptacle 40 of the cylindrical cover 32.

The stop unit 50 comprises a worm drive 52 which comprises a worm 54 and gearwheel 56 meshing therewith. The gearwheel 56 is connected to a screw 58 which extends in the longitudinal direction L. This screw 58 interacts with a stop sleeve 59 which projects into the hydraulic cylinder 42. This stop sleeve 59 can be displaced in the longitudinal direction by rotating the worm 54 which can be actuated from the outside.

The stop sleeve 59 serves as a stop for a hydraulic piston 46 which is partly situated in the interior of the hydraulic cylinder 42. The hydraulic piston 46 can be displaced in the longitudinal direction L, with an upward movement being effected by inserting hydraulic fluid into the annular space 44 and the interior space 43. In the process, the stop sleeve 59 ensures that the hydraulic piston 46 does not move too far toward the top. It follows that said sleeve limits the adjustment range of the hydraulic piston 46.

A flange-like section 66 is attached to the opposite end of the hydraulic piston 46, the diameter of said section in a planar view corresponding to the internal diameter of the cylindrical housing 20. It can clearly be seen from FIG. 2 that, in the cross section, this flange-like section 66 has a bowl-like shape, with a cylindrical actuation element 74 extending in the longitudinal direction L being attached to the base of this bowl.

FIG. 2 also shows that the cylindrical housing 20 holds a spring 68, in this case a helical spring, which is supported, on one end, on the flange-like section 38 of the housing 20 and, on the other end, on the flange-like section 66. The spring 68 ensures that the hydraulic piston 46 is pretensioned downward, with the flange-like section 66 butting against a lower base 70 inserted into the cylindrical housing 20. This base 70 has, with respect to the longitudinal axis L, a coaxial bore 72 through which the actuation element 74 engages. Additionally, a plurality of annular seals are provided within this bore 72.

At the lower end thereof, the base 70 has a bowl-shaped receptacle 86 which forms a hydraulic interior space 87. This hydraulic interior space is closed off toward the bottom by a clamp-type socket 80 such that it is sealed; it is possible to displace the clamp-type socket in the longitudinal direction within the receptacle 86 and said socket therefore forms a hydraulic piston 82. The clamp-type socket 80 has on its underside a cup-shaped clamping surface 84 which interacts with the ball and socket joint ball 16. The ball and socket joint ball 16 which is fixed to the adjacent holding arm 12.2 is situated in a ball and socket joint receptacle 18 of the holding arm 12.2, which is, for example, screwed to the base 70.

Using the clamp-type socket 80 and the clamping surface 84 thereof now affords the possibility of pressing the ball and socket joint ball 16 so hard into the ball and socket joint receptacle 18 that a movement of the two holding arms 12.1 and 12.2 in respect of one another is no longer possible.

The force required for the clamping is supplied by the spring 68 which moves the actuation element 74 into the hydraulic interior space 87. Since this interior space is filled by an incompressible medium and moreover is hermetically sealed, the movement of the actuation element 74 leads to a movement of the clamp-type socket in the same direction. However, a force transformation is obtained as a result of the smaller base area of the actuation element 74 compared to the base area of the clamp-type socket 80. The clamping force applied onto the ball and socket joint ball 16 by the clamp-type socket 80 is greater than the resilient force of the spring 68. However, in return, the displacement path of the actuation element 74 is correspondingly greater than the displacement path of the clamp-type socket 80.

To release the clamping, i.e. to move the clamp-type socket 80 upward, hydraulic fluid is inserted into the annular space 44 and then into the interior space 43 via the hydraulic connection 26. This moves the hydraulic piston 46 upward against the resilient force of the spring 68 and pulls the actuation element 74 out of the hydraulic interior space 87. This in turn leads to the clamp-type socket 80 being moved upward, but not—as already explained above—by the same amount as the actuation element 74.

The upward path of the hydraulic piston 46 is finally limited by the stop sleeve 59 and so the displacement path of the clamp-type socket 80, and thus the distance between the clamping surface 84 and the ball and socket joint ball 16, can be set to a minimum value with the aid of this adjustable stop sleeve 59. The advantage of this is that although the movement between holding arm 12.1 and holding arm 12.2 is possible just like that, the clamping itself can again be achieved very quickly because the displacement path of the clamp-type socket 80 is minimal.

FIG. 3 clearly shows this adjustment position of the clamp-type socket 80. In this position, the actuation element 74 is almost completely pulled out of the hydraulic interior space 87. In this position, the hydraulic piston 46 butts against the stop sleeve 59. As a result of the upward movement of the flange-like section 66, the spring 68 is compressed and this leads to the spring again pushing the flange-like section 66 downward once the hydraulic pressure is removed.

The figures also show that a screw attaches the ball and socket joint ball 16 to a component 90 which is placed, preferably screwed, onto the stop unit 50. In this case, the longitudinal axis of the screw used for the attachment to the component 90 runs at an angle to the longitudinal axis L.

Figure 4:
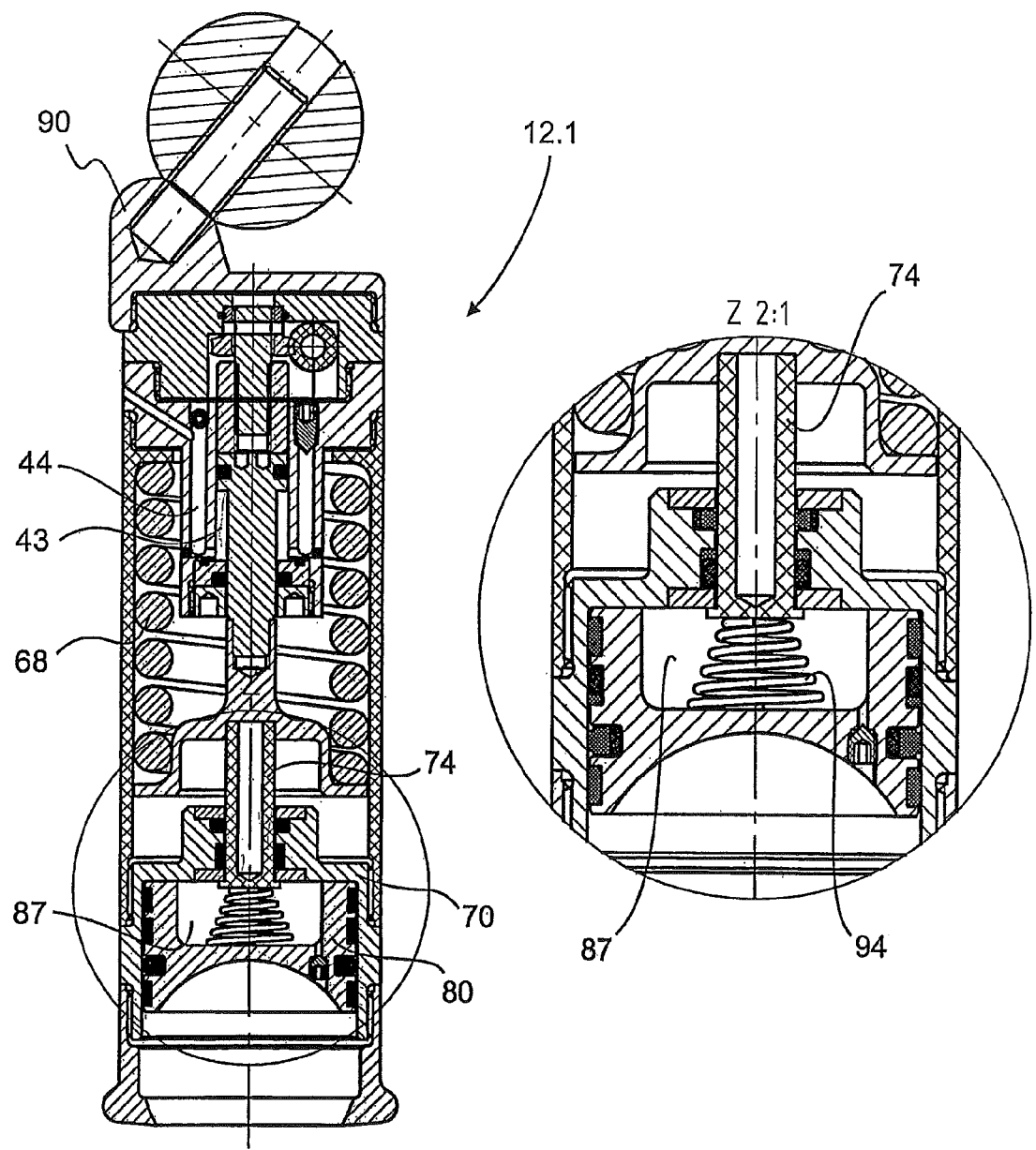
FIG. 4 shows a schematic sectional illustration of a holding arm in an opened state in accordance with an alternative refinement.

FIG. 4 illustrates an alternative refinement of the described holding arm 12.1 shown in FIG. 3. The difference consists of the fact that a spring 94, preferably a helical spring, is provided in the hydraulic interior space 87. This spring 94 is supported, on one end, on the actuation element 74 and, on the other end, on the clamp-type socket 80. The spring 94 is used to press the actuation element 74 back into the initial position, as illustrated in FIG. 4, when the spring 68 is tensioned.

The description above shows that the above-described internal design of a holding arm 12 corresponds to a connection device 10 which, on the one hand, can be easily adjusted and, on the other hand, provides the required clamping force to obtain a fixed clamping between adjacent holding arms. Thanks to the clamping force transformation apparatus, which is implemented by the hydraulic apparatuses formed by the actuation element 74, the hydraulic interior space 87 and the clamp-type socket 80, a very high clamping force can be achieved, even in the case of a spring 68 with small dimensions.

It is understood that the design shown in FIGS. 2 and 3 is purely of an exemplary nature and modifications or adaptations are by all means possible without departing from the scope defined by the claims.

What is claimed is:

1. A connection device for adjustably connecting a surgical apparatus, preferably a head support, which can be connected to a first end of the connection device to an attachment part on a stationary device, preferably an operating table, which can be connected to a second end of the connection device, the connection device having:
   a first holding arm,
   a second holding arm, connected to the first holding arm in a hinged fashion, with a ball and socket joint receptacle being assigned to the first holding arm and a ball and socket joint ball being assigned to the second holding arm, which together form a ball and socket joint,
   a clamping apparatus for the detachable clamping of the ball and socket joint ball in the ball and socket joint receptacle, the latter having a clamp-type socket which is assigned to the ball and socket joint ball and acted on by a clamping force via a pretensioning element in order to attain the clamping,
   a first hydraulic apparatus which can be actuated, is assigned to the clamping apparatus and, when operated, loads the clamping apparatus with a force opposing the clamping force, with the hydraulic apparatus having a hydraulic cylinder and a hydraulic piston which is arranged such that it can be displaced therein and connected to the clamping apparatus, and
   a clamping force transformation apparatus which is arranged between the pretensioning element and clamp-type socket and transforms the force applied by the pretensioning element into a larger clamping force acting on the clamp-type socket.

2. The connection device as claimed in claim 1, wherein the clamping force transformation apparatus has a second hydraulic apparatus with a cylinder and a piston which is arranged such that it can be displaced therein, with the clamp-type socket forming the piston, and
   the clamping apparatus has an actuation element which projects into the cylinder and the displacement of which causes a displacement of the clamp-type socket.

3. The connection device as claimed in claim 2, wherein provision is made for a spring between the actuation element and the clamp-type socket.

4. The connection device as claimed in claim 2, wherein the first hydraulic apparatus has a stop element which projects into the hydraulic cylinder and limits the displacement path of the piston.

5. The connection device as claimed in claim 4, wherein the stop element can be adjusted from the outside, the stop element having an outer tube-shaped section with a female thread and an inner section with a male thread which interact such that a rotation of the inner section displaces the outer section in the longitudinal direction.

6. The connection device as claimed in claim 5, wherein provision is made for a worm drive, the worm of which can be actuated from the outside and interacts with a gearwheel attached to the inner section of the stop element.

7. The connection device as claimed in claim 1, wherein the pretensioning element is a spring, in particular a helical spring.

8. The connection device as claimed in claim 7, wherein the clamping apparatus has a flange-like section on which one end of the spring is supported, while the other end of the spring is supported on the housing.

9. The connection device as claimed in claim 1, wherein each holding arm has a cylindrical housing in which the clamping apparatus and the first hydraulic apparatus are housed.

10. The connection device as claimed in claim 9, wherein the clamping apparatus has a flange-like section on which one end of the spring is supported, while the other end of the spring is supported on the housing.

11. The connection device as claimed in claim 1, wherein the ball and socket joint receptacle can be attached, in particular screwed, to one end of a holding arm.

12. The connection device as claimed in claim 11, wherein the ball and socket joint ball can be attached, in particular screwed, to the other end of a holding arm.

13. The connection device as claimed in claim 1, wherein at least three holding arms are interconnected in a hinged fashion.

14. The connection device as claimed in claim 1, wherein the first hydraulic apparatus can be connected to a pressure apparatus which can be operated by foot operation and generates the hydraulic pressure.

* * * * *